United States Patent
Mitsunaka et al.

(10) Patent No.: US 10,578,574 B2
(45) Date of Patent: Mar. 3, 2020

(54) SENSOR CIRCUIT

(71) Applicant: SHARP KABUSHIKI KAISHA, Sakai, Osaka (JP)

(72) Inventors: Takeshi Mitsunaka, Sakai (JP); Akira Saito, Sakai (JP); Nobuyuki Ashida, Sakai (JP); Kunihiko Iizuka, Sakai (JP)

(73) Assignee: SHARP KABUSHIKI KAISHA, Sakai, Osaka (JP)

(*) Notice: Subject to any disclaimer, the term of this patent is extended or adjusted under 35 U.S.C. 154(b) by 135 days.

(21) Appl. No.: 15/743,826

(22) PCT Filed: Jun. 2, 2016

(86) PCT No.: PCT/JP2016/066423
§ 371 (c)(1),
(2) Date: Aug. 10, 2018

(87) PCT Pub. No.: WO2017/010182
PCT Pub. Date: Jan. 19, 2017

(65) Prior Publication Data
US 2019/0025235 A1    Jan. 24, 2019

(30) Foreign Application Priority Data
Jul. 13, 2016 (JP) ................................. 2015-139937

(51) Int. Cl.
*G01N 27/22* (2006.01)
*G01R 27/26* (2006.01)
(Continued)

(52) U.S. Cl.
CPC ........... *G01N 27/223* (2013.01); *G01N 22/04* (2013.01); *G01N 27/228* (2013.01);
(Continued)

(58) Field of Classification Search
CPC .... G01N 27/223; G01N 27/228; G01N 22/04; G01R 33/1223; G01R 27/2658; G01R 27/2611; G01R 27/2605
(Continued)

(56) References Cited

U.S. PATENT DOCUMENTS

| 4,926,500 A * | 5/1990 | Tsuda ...................... H03D 7/165 |
| | | 455/302 |
| 2006/0203879 A1* | 9/2006 | Ruttiger ............. B60H 1/00785 |
| | | 374/142 |

(Continued)

FOREIGN PATENT DOCUMENTS

| JP | 2007-505302 A | 3/2007 |
| JP | 2008-203157 A | 9/2008 |

OTHER PUBLICATIONS

C. Sideris, A. Hajimiri, "An Integrated magnetic Spectrometer for Multiplexed Biosensing", IEEE Solid-State Circuit Conf. Dig. Tech. papers, pp. 300 to 302, Feb. 2013.

(Continued)

*Primary Examiner* — Melissa J Koval
*Assistant Examiner* — Trung Nguyen
(74) *Attorney, Agent, or Firm* — ScienBiziP, P.C.

(57) ABSTRACT

Provided is a technology for detecting a change in an inspection target containing moisture. A sensor circuit (1) for inspecting property of an inspection target includes an oscillator (20) having a resonance frequency of 30 to 200 GHz, and a detection circuit (3) that estimates an oscillation frequency of the oscillator.

5 Claims, 9 Drawing Sheets

(51) Int. Cl.
    *G01N 22/04* (2006.01)
    *G01R 33/12* (2006.01)
(52) U.S. Cl.
    CPC ...... *G01R 27/2605* (2013.01); *G01R 27/2611* (2013.01); *G01R 27/2658* (2013.01); *G01R 33/1223* (2013.01)
(58) Field of Classification Search
    USPC .... 324/425, 436, 442, 76.11, 136, 327, 300, 324/310, 315, 364, 500, 520, 600, 633, 324/667, 674; 73/861.27, 335.04, 74, 73/24.06, 579, 657
    See application file for complete search history.

(56) References Cited

U.S. PATENT DOCUMENTS

2009/0267596 A1    10/2009  Wang et al.
2013/0082785 A1*    4/2013  Afshari .................. H03B 28/00
                                                        331/48

OTHER PUBLICATIONS

H. Yada, M. Nagai, K. Tanaka, "Origin of the fast relaxation component of water and heavy water revealed by terahertz time-domain attenuated total reflection spectroscopy", Chemical Physics Letters, pp. 166 to 170, 2008.

M. Abidi et al., Sensing Liquid Properties Using Split-Ring Resonator in Mn-wave Band, IECON 2010—36th Annual Conference on IEEE Industrial Electronics Society, 2010, pp. 1289-1301.

* cited by examiner

FIG. 9
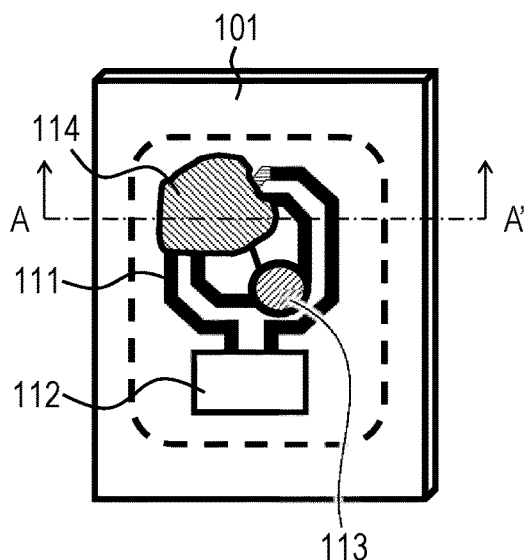
(a)
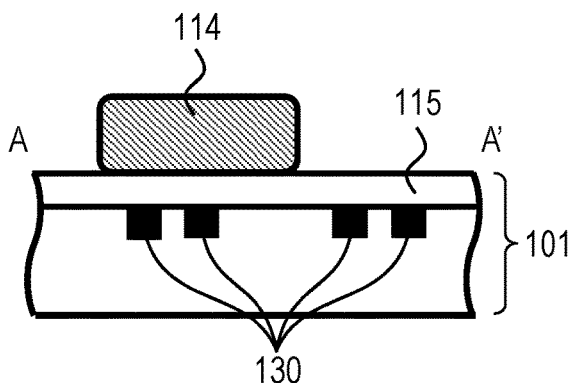
(b)
| 101: SEMICONDUCTOR SUBSTRATE | 114: INSPECTION TARGET |
| 111: INDUCTOR | 115: PROTECTION FILM |
| 112: OTHER CIRCUITS | 130: HIGHEST METAL LAYER |
| 113: MAGNETIC PARTICLE | |

SENSOR CIRCUIT

TECHNICAL FIELD

The present invention relates to a sensor circuit that includes a high-frequency oscillator and detects a change in an inspection target containing moisture.

BACKGROUND ART

Cost reduction, miniaturization, inspection time reduction, simplicity of operation, and the like are required for diagnostic equipment for a human body used at home, a simple diagnostic facility or the like. A sensor IC (integrated circuit: semiconductor integrated circuit) formed on a semiconductor integrated circuit can satisfy such a requirement.

For example, an example of a sensor IC formed on a semiconductor integrated circuit is disclosed in PTL 1. FIGS. 7 to 9 are diagrams for explaining the sensor IC according to PTL 1.

FIG. 7(a) is a diagram illustrating a circuit configuration of the sensor IC. As illustrated in FIG. 7(a), the sensor IC includes oscillators 110 and 120 having inductors 111 and 121 formed on a metal layer (metal layer) on a semiconductor substrate 101. FIG. 7(b) is a diagram illustrating an example in which the circuit illustrated in FIG. 7(a) is mounted on the semiconductor substrate 101. As illustrated in FIG. 7(b), the oscillators 110 and 120 are provided in a row. For the simplicity, transistors, capacitors, and the like are represented as other circuits 112 and 122.

FIG. 8(a) is a diagram illustrating a state in which a magnetic particle 113 and an inspection target 114 are brought into contact with the inductor 111. As illustrated in FIG. 8(a), when the inspection target 114 is brought into contact with the semiconductor substrate 101 illustrated in FIG. 7(b), a magnetic permeability changes due to the fluctuation of the magnetic particle 113 attached to the inspection target 114, and inductances of the inductors 111 and 121 are affected by the change of the magnetic permeability. As a result, the oscillation frequencies output by the oscillators 110 and 120 change, and a detector (not illustrated) detects the change in the oscillation frequency. The change in the oscillation frequency indicates the variation in the properties of the inspection target 114.

For example, the oscillator 110 is to be used as a sensor portion among the oscillators 110 and 120, and thus, the inspection target 114 is selectively brought into contact with the oscillator 110. FIG. 8(b) is a diagram illustrating a state in which an inspection target 124 is further brought into contact with the inductor 121 comparing with the state illustrated in FIG. 8(a). The other oscillator 120 is to be used as a reference portion, and thus, the other oscillator 120 may not be brought into contact with the inspection target or may be brought into contact with the inspection target 124 used as a reference as illustrated in FIG. 8(b). In this way, the property difference of the inspection target 114 can be evaluated by checking a difference in the oscillation frequencies of the oscillators 110 and 120 using an enable signal or a /enable signal.

FIG. 9(a) is a view illustrating a position of a cross section A-A' of the semiconductor substrate 101. FIG. 9(b) is a cross-sectional view illustrating the cross section A-A' of the semiconductor substrate 101. As illustrated in FIG. 9(b), even if the inductor 111 formed on the metal layer formed on the highest metal layer 130 in the semiconductor substrate 101, since a protection film 115 formed of an insulator or the like is formed between the surface of the semiconductor substrate 101 and the inductor 111, the inspection target 114 does not come in contact with the highest metal layer 130. The above description is similarly applicable to the inductor 121.

However, in the sensor IC disclosed in PTL 1 and NPL 1, it is necessary to connect the magnetic particle 113 to the inspection target 114 which is brought into contact with the semiconductor substrate 101. According to NPL 1, the frequency variation due to the variation of the magnetic particle 113 is proportional to the magnetic susceptibility $\chi$. The magnetic susceptibility $\chi$ is a ratio of H to the magnetic polarization Pm generated in the magnetic material when the external magnetic field H is applied. As illustrated in FIG. 16.8.1, the magnetic particle in NPL 1 becomes positive at a frequency lower than 2 GHz, and the magnetic polarization becomes opposite to the external magnetic field. Furthermore, in the figure, there is almost no variation at higher frequencies such as exceeding 10 GHz.

CITATION LIST

Patent Literature

PTL 1: U.S. Patent Application Publication No. 2009/0267596 (published on Oct. 29, 2009)

Non Patent Literature

NPL 1: C. Sideris, A. Hajimiri, "An Integrated magnetic Spectrometer for Multiplexed. Biosensing", IEEE Solid-State Circuit Conf. Dig. Tech. papers, pp. 300 to 302, February 2013

NPL 2: H. Yada, M. Nagai, K. Tanaka, "Origin of the fast relaxation component of water and heavy water revealed by terahertz time-domain attenuated total reflection spectroscopy", Chemical Physics Letters, pp. 66 to 170, 2008

SUMMARY OF INVENTION

Technical Problem

In an aqueous solution, it is known that a hydration phenomenon occurs in which water molecules are bound by solutes due to ionization of a solute into ions in a case of a solute of an electrolyte such as NaCl, and via an electrostatic force or hydrogen bond caused by a polarization bias in the solute molecules in a case of a solute of a non-electrolyte such as sugar. The hydration phenomenon is also greatly related to the activity of macromolecules such as proteins. In the aqueous solution, the bulk water (water in a state of not being bound because separated enough from the solute) decreases by replacing trio water molecule with a protein, and thus, the dielectric constant of the bulk water changes to the dielectric constant of the protein. A graph indicating the complex dielectric constant of bulk water is illustrated in FIG. 2 of NPL 2. Due to the relaxation phenomenon of the bulk water, particularly, the variation of the complex dielectric constant s large at the frequency region of 30 GHz to 200 GHz. It can be understood that the complex dielectric constant also varies at the above frequency region when the amount of bulk water varies.

The sensor IC disclosed in PTL 1 and NPL 1, the motion of the water molecules in the bulk water cannot be evaluated because the evaluation frequency is 3.3 GHz, and the hydration state cannot be expressed. This is because the motion of the water molecules is as large as the frequency of approximately 10 GHz or more. For this reason, by adding a magnetic particle to the sample and evaluating the motion at the frequency of 3.3 GHz suitable for the frequency variation of the magnetic particle, it is possible to check the operation of the sample. Therefore, it is necessary to add a magnetic particle.

The present invention has been made in view of the above problems, and an object thereof is to provide a technology for detecting a change in an inspection target containing moisture.

Solution to Problem

In order to solve the problems described above, a sensor circuit according to an aspect of the invention is a sensor circuit that inspects property of an inspection target, and includes an oscillation unit having a resonance frequency of 30 to 200 GHz, and an estimation unit that estimates the oscillation frequency of the oscillation unit.

Advantageous Effects of Invention

According to an aspect of the invention, it is possible to detect a change of an inspection target containing moisture by replacing the change of the inspection target with change of bulk water.

BRIEF DESCRIPTION OF DRAWINGS

FIG. 1(a) illustrates a configuration of as oscillator in the present embodiment and FIG. 1(b) illustrates a configuration of a sensor circuit in the present embodiment.

FIG. 3(a) illustrates a configuration of an oscillator in the present embodiment and FIG. 3(b) illustrates a configuration of a sensor circuit in the present embodiment.

FIG. 5(a) illustrates a schematic configuration of a sensor device according to the present embodiment, FIG. 5(b) illustrates a state in which the inspection target is brought into contact with the resonator, and FIG. 5(c) illustrates the oscillation frequency of an oscillator 20 in this state.

FIG. 6(a) illustrates a state in which the inspection target is brought into contact with the resonator and FIG. 6(b) illustrates the oscillation frequency of the oscillator 20 in this state.

FIG. 7(a) illustrates a configuration of a circuit of the sensor IC and FIG. 7(b) illustrates an example in which the circuit is mounted on a semiconductor substrate 101.

FIG. 8(a) illustrates a state in which a magnetic particle and an inspection target are brought into contact with an inductor and FIG. 8(b) illustrates a state in which the inspection target is brought into contact with an inductor in addition to this state.

FIG. 9 is a diagram for describing a semiconductor substrate in PTL 1, and FIG. 9(a) illustrates a position of a cross section. A-A' of the semiconductor substrate and FIG. 9(b) is a cross sectional diagram illustrating the cross section A-A' of the semiconductor substrate.

DESCRIPTION OF EMBODIMENTS

Figure 1:
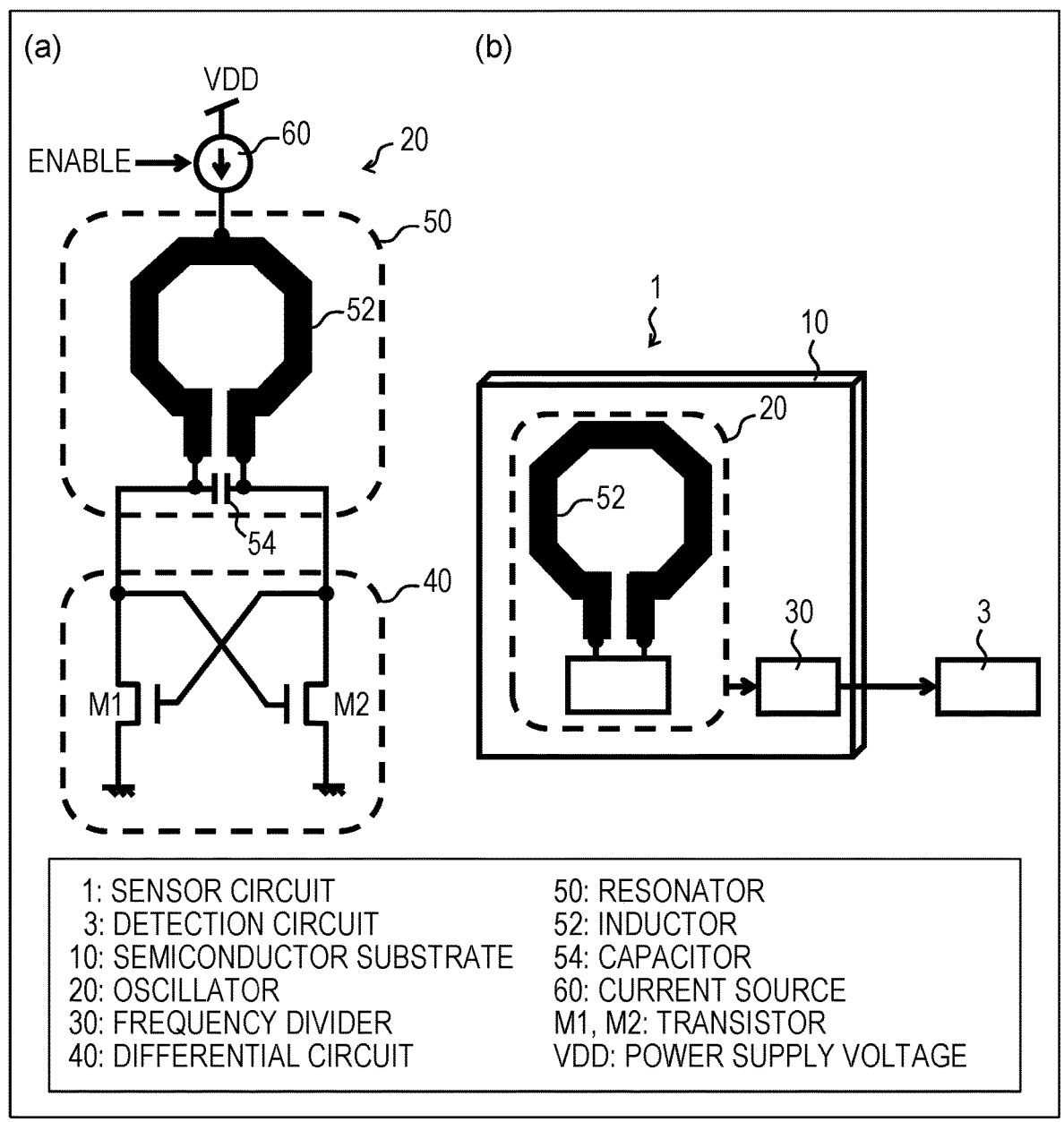
FIG. 1 is a block diagram illustrating a sensor circuit according to an embodiment 1 of the invention.

Hereinafter, embodiments of the invention will be described in detail. However, the configurations described in the embodiment are not intended to limit the scope of the present invention unless otherwise specified, and are merely illustrative examples. In the drawings described below, the same reference numerals will be given to those having the same function, and the description thereof will not be repeated and will be omitted.

The sensor circuit according to the embodiments of the invention is a sensor IC (integrated circuit: semiconductor integrated circuit) in which an inspection target is brought into contact with a surface of a semiconductor substrate, and detects a changes of a dielectric constant and a magnetic permeability which change when the dielectric constant and the magnetic permeability of the inspection target or the properties of inspection target change.

Embodiment 1

First, a sensor circuit 1 according to an embodiment 1 of the invention will be described with reference to FIG. 1. FIG. 1(a) is a block diagram illustrating a configuration of an oscillator 20 according to the present embodiment. FIG. 1(b) is a block diagram illustrating a configuration of the sensor circuit 1 according to the present embodiment.

(Configuration of Oscillator)

As illustrated in FIG. 1(a), the oscillator (oscillation unit) 20 includes a differential circuit 40, a resonator 50 formed between a differential operations of the differential circuit 40, and a current source 60 that controls the driving of the oscillator 20 according to control signals (enable and /enable). The oscillator 20 has any one of resonance frequencies of 30 to 200 GHz. The frequency of 30 to 200 GHz is a frequency in which the change of the complex dielectric constant of water is large, and thus, the change of the frequency characteristics of the dielectric constant can be detected with high sensitivity.

The differential circuit 40 includes an NMOS transistor M1 and an NMOS transistor M2 that are cross-coupled to each other. Another differential circuit may be used as appropriate. For example, a bipolar transistor may be used.

The resonator 50 includes an inductor 52 and a capacitor 54 connected in parallel between differential operations of the differential circuit 40. The resonance frequency at which the resonator 50 resonates is the oscillation frequency at which the oscillator 20 oscillates. Since the resonator 50 is not an antenna in a narrow sense which transmits and receives electromagnetic waves, the aperture diameter is not limited by the wavelength. Therefore, the size of the resonator 50 canal be set to equal to or smaller than 200 μm square (a size that falls within a square having sides of 200 μm) which is smaller than the quarter wavelength approximately 1.5 mm of the electromagnetic wave of 200 GHz.

The inductor 52 is formed on the highest layer (the layer closest to the contact position of the substrate and the inspection target) among of the metal layers of the semiconductor substrate 10. The inductor 52 occupies most of the circuit size of the resonator 50. In addition, the resonator 50 occupies most of the circuit size of the oscillator 20. In the present embodiment, the area of the inductor 52 is determined in such a manner that the size of the resonator 50 in the plan view falls within a square having sides of 200 μm. The capacitor 54 may be formed by gate capacitances of the transistors M1 and M2 or the parasitic capacitance (not illustrated) of the wiring.

The inductor 52 and the capacitor 54 form an LC circuit, and the resonance frequency of the resonator 50 and the oscillation frequency of the oscillator 20 are determined by the inductance of the inductor 52 and the capacitance of the capacitor 54.

In this case, the oscillation frequency f of the oscillator 20 is expressed by Expression 1 below.

$$f=1/\{2\pi\sqrt{(LC)}\} \quad \text{Expression 1}$$

Here, L is an inductance value (the number of flux linkage/current) of the inductor 52, C is a sum of the capacitance (electric capacitance) of the capacitor 54 and a reference parasitic capacitance applied the inductor 52 when mounting the inspection target 70. The inductance and the capacitance are determined such that the oscillator 20 oscillates at a frequency of 30 GHz to 200 GHz.

For example, in a case where the inductance of the inductor 52 is around 1 nH and the capacitance of the capacitor 54 is around 27 fF, the resonance frequency of the resonator 50 and the oscillation frequency of the oscillator 20 are around 30 GHz.

(Configuration of Sensor Circuit)

As illustrated in FIG. 1(b), the sensor circuit 1 includes an oscillator 20, a frequency divider 30, and a detection circuit (an estimation unit) 3. At least the oscillator 20 and the frequency divider 30 are formed on the same semiconductor substrate 10. The detection circuit 3 may be formed on the semiconductor substrate 10 or may be formed on a member different from the semiconductor substrate 10, for example, a commercially available microcomputer or the like (not illustrated) may be substituted.

The frequency divider 30 is a frequency divider that divides the oscillation frequency oscillated by the oscillator 20 and outputs an output signal having the division-resultant frequency to the detection circuit 3. A division ratio of the frequency divider 30 is 1/N (N is a rational number of equal to or greater than 1). The frequency divider 30 sets the frequency of the signal input to the detection circuit 3 to 1/N times of the oscillation frequency of the oscillator 20 such that the detection circuit 3 can easily handle the signal input to the detection circuit 3. As a result, the frequency of the signal input to the detection circuit 3 falls within the frequency band in which the detection circuit 3 operates. The frequency divider 30 is not an essential configuration for solving the problem in the invention.

The detection circuit 3 calculates the oscillation frequency of the oscillator 20 from the frequency output from the frequency divider 30 and the division ratio 1/N of the frequency divider 30. That is, the detection circuit 3 estimates the oscillation frequency of oscillator 20 by counting the signals input in a predetermined period (for example, 100 msec or the like), and integrating the inverse number N of the division ratio of the frequency divider 30 and 1 second/predetermined period to the counted value referring to the output signal of the frequency divider 30. The detection circuit 3 includes a counter circuit for counting a change in frequency of a signal output from the frequency divider 30 for a predetermined period.

(Estimation of Oscillation Frequency)

Figure 2:
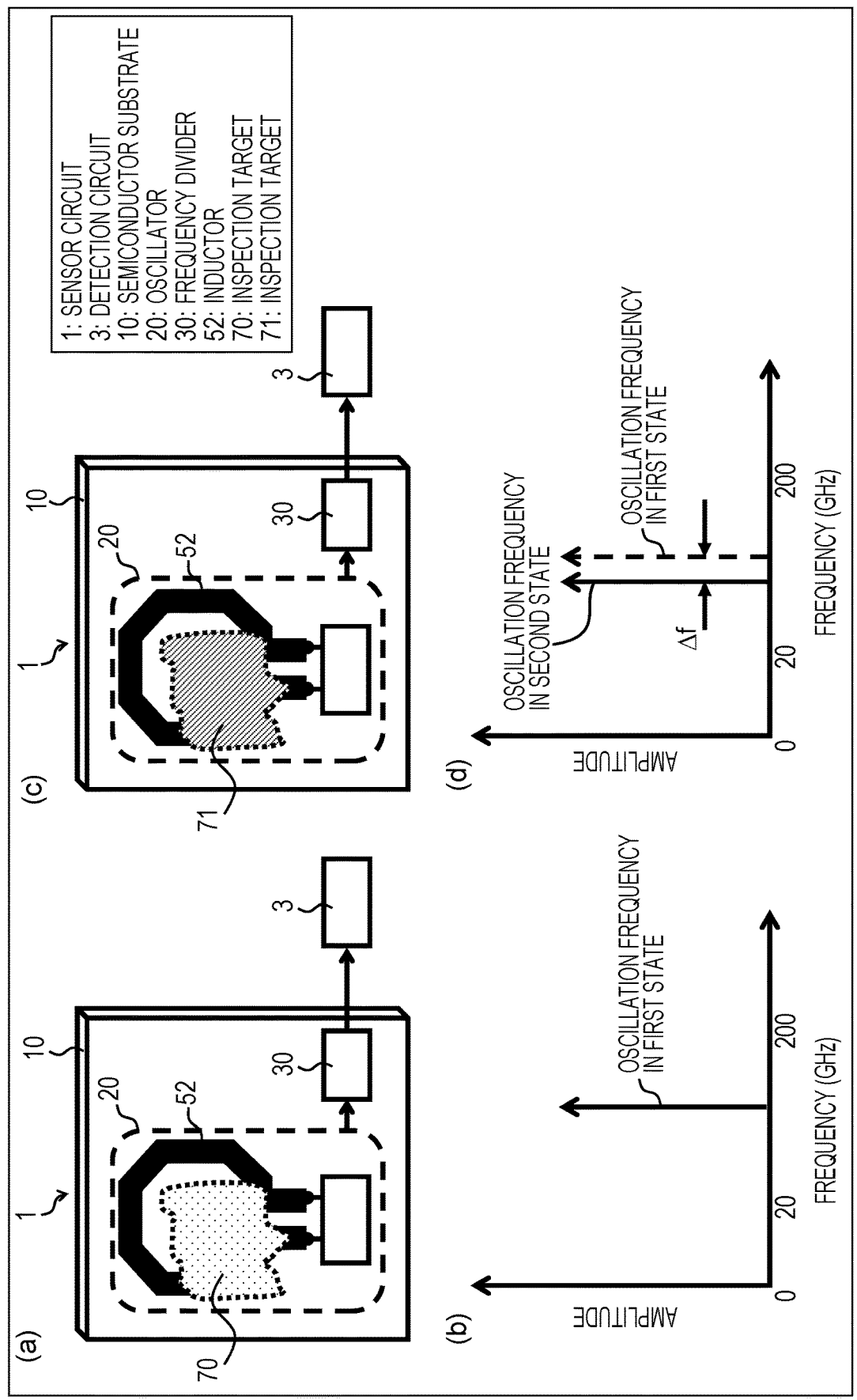
FIG. 2 is a diagram illustrating a method of estimating an oscillation frequency by bringing an inspection target according to the embodiment 1 of the invention into contact with a semiconductor substrate, and FIGS. 2(a) and (c) illustrate a state in which the inspection target is brought into contact with an inductor and FIGS. 2(b) and (d) illustrate the oscillation frequency of the oscillator in each state.

FIG. 2 is a diagram illustrating a method of estimating the oscillation frequency by bringing the inspection target into contact with a semiconductor substrate. FIGS. 2(a) and 2(c) illustrate a state in which inspection targets 70 and 71 are brought into contact with an inductor 52. FIGS. 2(b) and 2(d) illustrate the oscillation frequencies of the oscillator 20 in respective states illustrated in FIGS. 2(a) and 2(c). The inspection targets 70 and 71 contain moisture.

As illustrated in FIG. 2(a), the user brings the inspection target 70 of which the property is not changed (a first state) into contact with the vicinity of the region where the inductor 52 is formed, on the semiconductor substrate 10. Next, the user causes an enable signal to be output to the oscillator 20 from the current source 60.

As a result, the oscillator 20 starts an operation and oscillates at the oscillation frequency in the first state illustrated in FIG. 2(b). The oscillation frequency of the oscillator 20 is divided into 1/N frequency by the frequency divider 30 and counted for a predetermined period by the detection circuit 3. Then, the detection circuit 3 estimates that the oscillation frequency of the oscillator 20 is the frequency in the first state illustrated in FIG. 2(b), and holds the value of the frequency as a reference frequency.

Thereafter, the property of the inspection target 70 changes to the property of the inspection target 71 (a second state) as illustrated in FIG. 2(c), and as a result thereof, the dielectric constant of the water contained in the inspection target 70 changes to the dieletric constant of the water contained in the inspection target 71. In the second state, the user causes an enable signal to be output to the oscillator 20 from the current source 60. As a result, the oscillator 20 starts the operation and oscillates at the oscillation frequency in the second state as illustrated in FIG. 2(d). Similarly to that in the first state, the oscillation frequency of the oscillator 20 in the second state is also divided into 1/N frequency by the frequency divider 30 and counted for a predetermined period by the detection circuit 3. Then, the detection circuit 3 estimates that the oscillation frequency of the oscillator 20 is the frequency in the second state illustrated in FIG. 2(d).

As the property of the inspection target 70 changes to that of the inspection target 71, the dielectric constant of the water contained in the inspection targets changes. Next, when the dielectric constant (ε) changes, the parasitic capacitance component of the inductor 52 applied to the inductor 52 of the oscillator 20 among the capacitance C changes. This is apparent from an expression C=ε×d/S (d: thickness of the dielectric, S: area of the dielectric). A difference ΔC of the capacitance value C corresponding to the sum of the capacitance of the capacitor 54 and the parasitic capacitance value before and after the changes of the property appears as a difference Δf of the oscillation frequency of the oscillator 20. The relational expression between the difference Δf and the difference ΔC is expressed in following Expression 2.

$$\Delta f=1/[2\pi\sqrt{\{L(C+\Delta C)\}}]-1/\{2\pi\sqrt{(LC)}\} \quad \text{Expression 2}$$

(Effects)

The user can estimate that the property of the inspection target 70 is changed to the property of the inspection target 71 by checking the difference Δf between the reference oscillation frequency in the first state and the oscillation frequency of the oscillator 20 in the second state. An information processing device (a detection unit) may acquire the oscillation frequency of the oscillator 20 estimated by detection circuit 3, and may detect the change in the property of the inspection target with reference to the difference Δf (change of the oscillation frequency), and furthermore, the user may be notified of the change in the property of inspection target by sending an alarm or the like.

Embodiment 2

Figure 3:
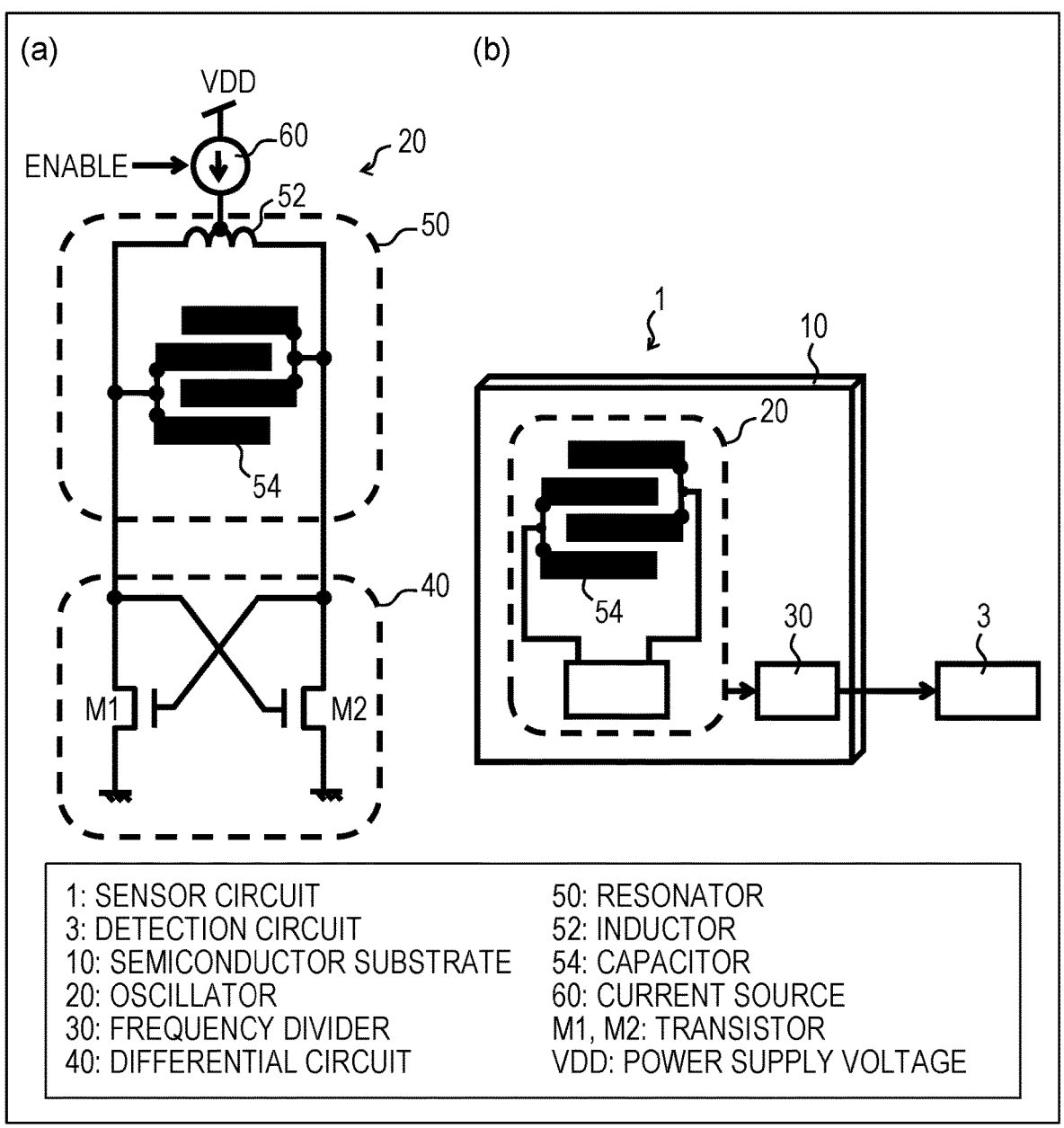
FIG. 3 is a block diagram illustrating a sensor circuit according to an embodiment 2 of the invention.

Next, a sensor circuit 1 according to an embodiment of the invention will be described with reference to FIG. 3. FIG. 3(a) is a block diagram illustrating configuration of an oscillator 20 according to the present embodiment. FIG. 3(b) is a block diagram illustrating the configuration of the sensor circuit 1 according to the present embodiment. The configurations of the inductor 52 and the capacitor 54 are different compared to the embodiment 1 of the invention.

(Configuration of Oscillator and Sensor Circuit)

The oscillator 20 includes a differential circuit 40, a resonator 50 formed between the differential operations of the differential circuit 40, and a current source 60 that controls the driving of the oscillator 20 according to a control signal. The oscillator 20 has any one of the resonance frequencies of 30 to 200 GHz.

In the configuration illustrated in FIGS. 3(a) and 3(b), the capacitor 54 is formed on the metal layer which is the highest layer among the metal layers of the semiconductor substrate 10. In addition, in a plan view, the capacitor 54 is formed in a comb shape on a most of the area occupied by the oscillator 20 on the semiconductor substrate 10.

In addition, the inductor 52 may be formed on a metal layer which is not the highest layer, or may be an active inductor or the like formed of a transistor.

Since the capacitor 54 is formed on the metal layer which is the highest layer, the capacitance of the capacitor 54 changes by the moisture attached to the surface of the semiconductor substrate 10 and the inspection target. Then, the oscillation frequency oscillated by the oscillator 20 changes.

(Estimation of Oscillation Frequency)

Figure 4:
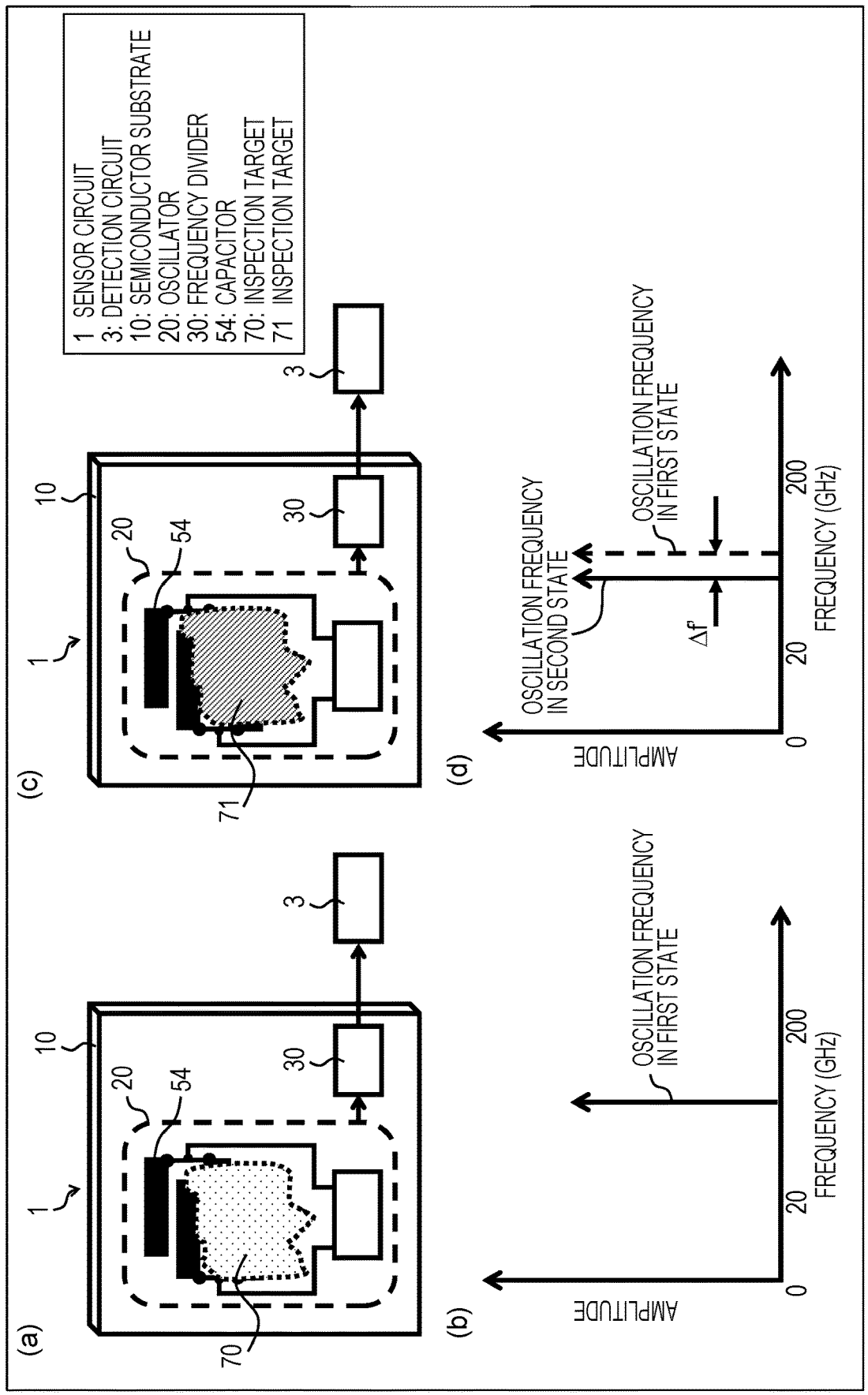
FIG. 4 is a diagram illustrating a method of estimating an oscillation frequency by bringing the inspection target according to the embodiment 2 of the invention into contact with a semiconductor substrate, and FIGS. 4(a) and (c) illustrate a state in which the inspection target is brought into contact with a capacitor and FIGS. 4(b) and (d) illustrate the oscillation frequency of the oscillator in each state.

FIG. 4 is a diagram illustrating a method of estimating an oscillation frequency by bringing an inspection target into contact with a semiconductor substrate. FIGS. 4(a) and 4(c) respectively illustrate a state in which the inspection targets 70 and 71 are brought into contact with the capacitor 54. FIGS. 4(b) and 4(d) illustrate the oscillation frequency of the oscillator 20 in the state illustrated in FIGS. 4(a) and 4(c), respectively. The inspection targets 70 and 71 contain moisture.

As illustrated in FIG. 4(a), the user brings the inspection target 70 of which the property is not changed (a first state) into contact with the vicinity of the region where the capacitor 54 is formed, on the semiconductor substrate 10. The capacitor 54 is formed as a comb shape capacitor. In addition, the capacitor 54 is formed by a capacitor formed on a metal layer which is the highest layer. Next, the user causes an enable signal to be output to the oscillator 20 from the current source 60.

As a result, the oscillator 20 starts an operation and oscillates at the oscillation frequency in the first state illustrated in FIG. 4(b). The oscillation frequency of the oscillator 20 is divided into 1/N frequency by the frequency divider 30 and counted for a predetermined period by the detection circuit 3. Then, the detection circuit 3 estimates that the oscillation frequency of the oscillator 20 is the frequency in the first state illustrated in FIG. 4(b), and holds the value of the frequency as a reference frequency.

Thereafter, the property of the inspection target 70 changes to the property of the inspection target 71 (a second state) as illustrated in FIG. 4(c), and as a result thereof, the dielectric constant of the water contained in the inspection target 70 changes to the dielectric constant of the water contained in the inspection target 71. In the second state, the user causes an enable signal to be output to the oscillator 20 from the current source 60. As a result, the oscillator 20 starts the operation and oscillates at the oscillation frequency in the second state as illustrated in FIG. 4(d). Similarly to that in the first state, the oscillation frequency of the oscillator 20 in the second state is also divided into 1/N frequency by the frequency divider 30 and counted for a predetermined period by the detection circuit 3. Then, the detection circuit 3 estimates that the oscillation frequency of the oscillator 20 is the frequency in the second state illustrated in FIG. 4(d).

As the property of the inspection target 70 changes to that of the inspection target 71, the dielectric constant of the water contained in the inspection targets changes. When the dielectric constant of the inspection target changes, the capacitance C of the capacitor 54 of the oscillator 20 changes. Then, the difference ΔC of the capacitance C before and after the property change appears as the difference Δf' of the oscillation frequency of the oscillator 20. The relational expression between the difference Δf' and the difference ΔC is expressed in following Expression 3.

$$\Delta f' = 1/[2\pi\sqrt{\{L(C+\Delta C)\}}] - 1/\{2\pi\sqrt{(LC)}\} \quad \text{Expression 3}$$

(Effects)

The user can estimate that the property of the inspection target 70 is changed to the property of the inspection target 71 by checking the difference Δf' between the reference oscillation frequency in the first state and the oscillation frequency of the oscillator 20 in the second state. An information processing device (a detection unit) may acquire the oscillation frequency of the oscillator 20 estimated by detection circuit 3, and may detect the change in the property of the inspection target with reference to the difference Δf' (change of the oscillation frequency), and furthermore, the user may be notified of the change in the property of inspection target by sending an alarm or the like.

It is known that the frequency region of 30 GHz to 200 GHz is a frequency region in which influences of both two dielectric relaxations of water (fast relaxation: peak is about 640 GHz and slow relaxation: peak is about 20 GHz) are easily seen. Due to this, the change of the complex dielectric constant with respect to the change of the state of the water molecule is large. Since the change of the complex dielectric constant can be detected as a change in dielectric constant, eventually as a change in frequency by realizing a sensor circuit in which the electromagnetic field appearing from the surface such as the resonator 50 influences the motion of the water molecule, the variation of the inspection target containing moisture can be detected. In this case, it is not necessary to use magnetic particle, which leads to simplification of the frequency measurement. Therefore, it is very effective to realize a sensor circuit that performs the detection using radio waves with a frequency of 30 GHz to 200 GHz.

Embodiment 3

An embodiment 3 of the invention will be described with reference to FIGS. 5 and 6. For the convenience of the description, the same reference numerals will be given to members having the same functions as those described in the above embodiment, and the description thereof will be omitted.

In the embodiments 1 and 2 described above, the case where the inspection targets 70 and 71 come in contact with a part of the surface of the sensor circuit 1 has been described. In the embodiment 3, a case where an entire surface of the sensor device 2 including the semiconductor substrate 10 is immersed in the aqueous solution (inspection targets 76 and 77) will be described.

(Configuration of Sensor Device)

FIG. 5(a) is a perspective view illustrating a schematic configuration of a sensor device 2 according to the present embodiment.

The sensor device 2 is an integrated circuit (IC) used for sensors. The sensor device 2 includes a semiconductor substrate 10 and a sealing material 16.

In the semiconductor substrate 10, an oscillator 20 including a resonator 50 is formed. The oscillator 20 has a resonance frequency of 30 to 200 GHz. The resonator 50 is formed so as to appear on the surface of the semiconductor substrate 10.

The sealing material 16 seals bonding wires and bonding pads and the like such that the bonding wires and the bonding pads and the like (not illustrated) are not in direct contact with the aqueous solution. On the other hand, the sealing material 16 includes a window through which the inspection target comes in contact with the surface of the resonator 50. The material and shape of the sealing material 16 are not particularly limited.

The sensor device 2 may have any shape as long as the inspection target does not approach or does not come in contact with other than the surface of the resonator 50 in the sealing material 16. The inspection target 77 is an aqueous solution in which the inspection target 76 has been changed. The change from the inspection target 76 to the inspection target 77 is a change in the property of the aqueous solution due to, for example, solute change over the time (change in concentration, progress of vaporization, solidification, chemical reaction, or the like).

(Estimation of Oscillation Frequency)

Figure 5:
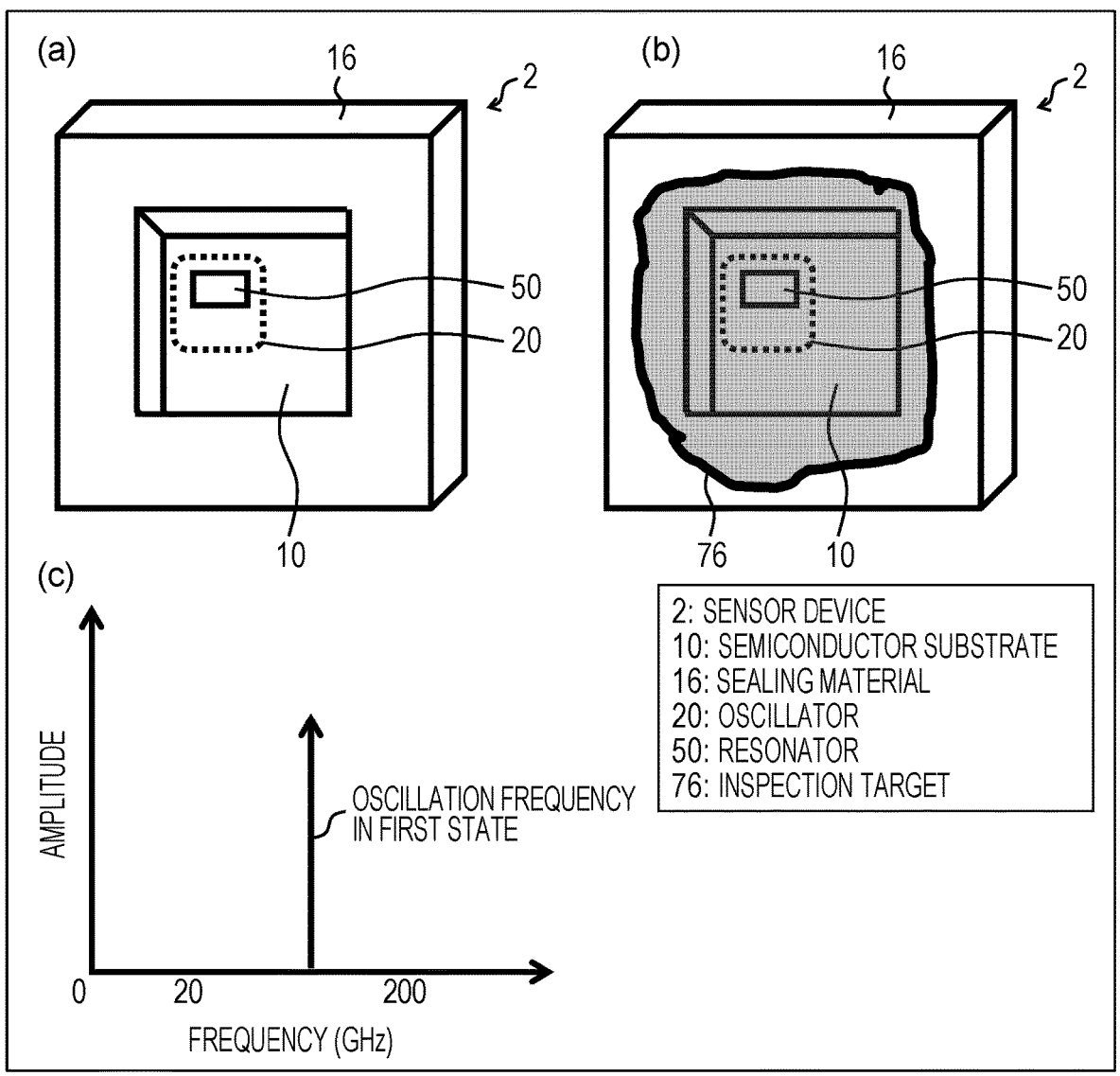
FIG. 5 is a diagram illustrating a method of estimating an oscillation frequency by bringing an inspection target according to an embodiment 3 of the invention into contact with a semiconductor substrate.
Figure 6:
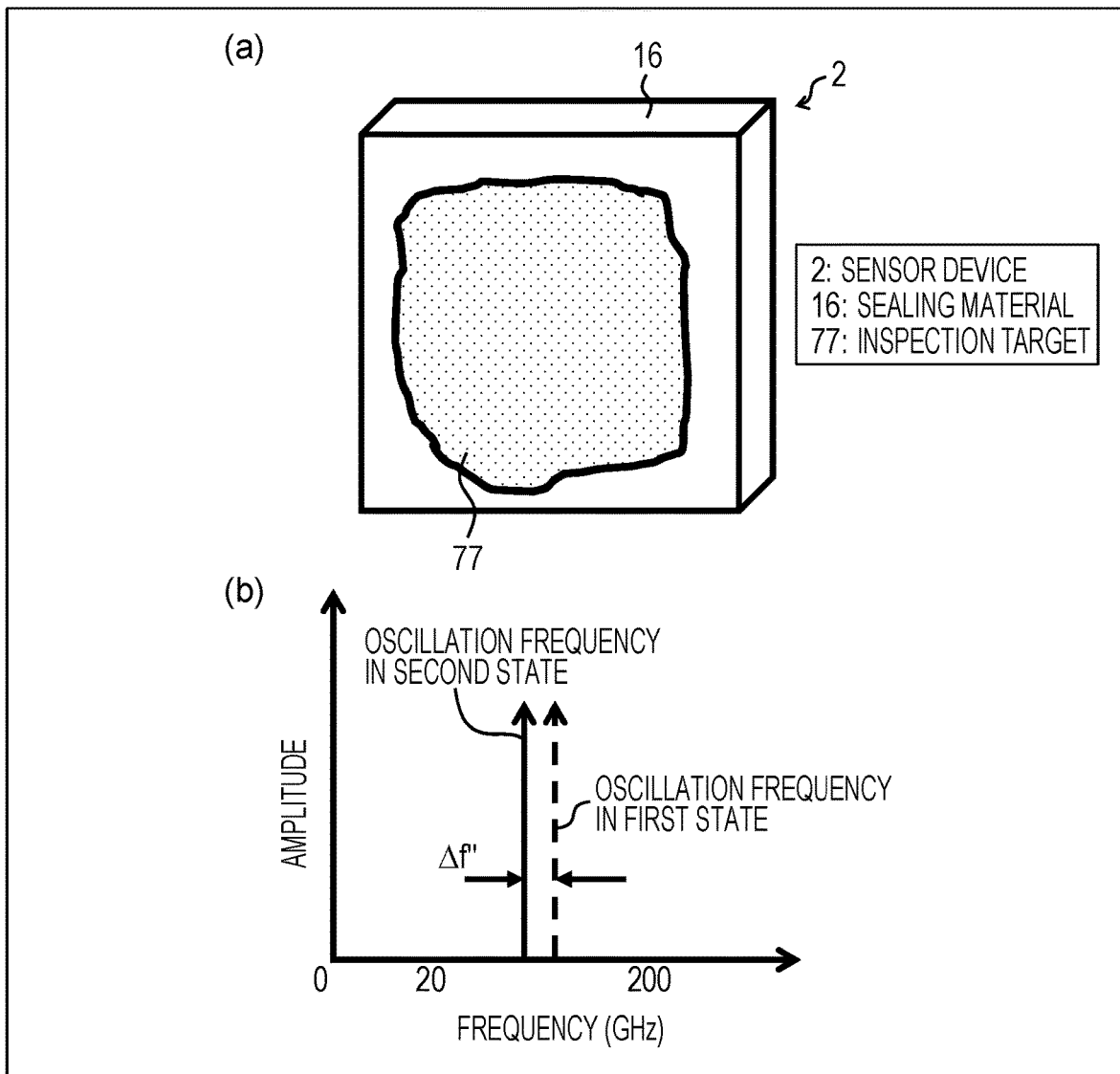
FIG. 6 is a diagram illustrating a method of estimating the oscillation frequency by bringing the inspection target according to the embodiment 3 of the invention into contact with a semiconductor substrate.
Figure 7:
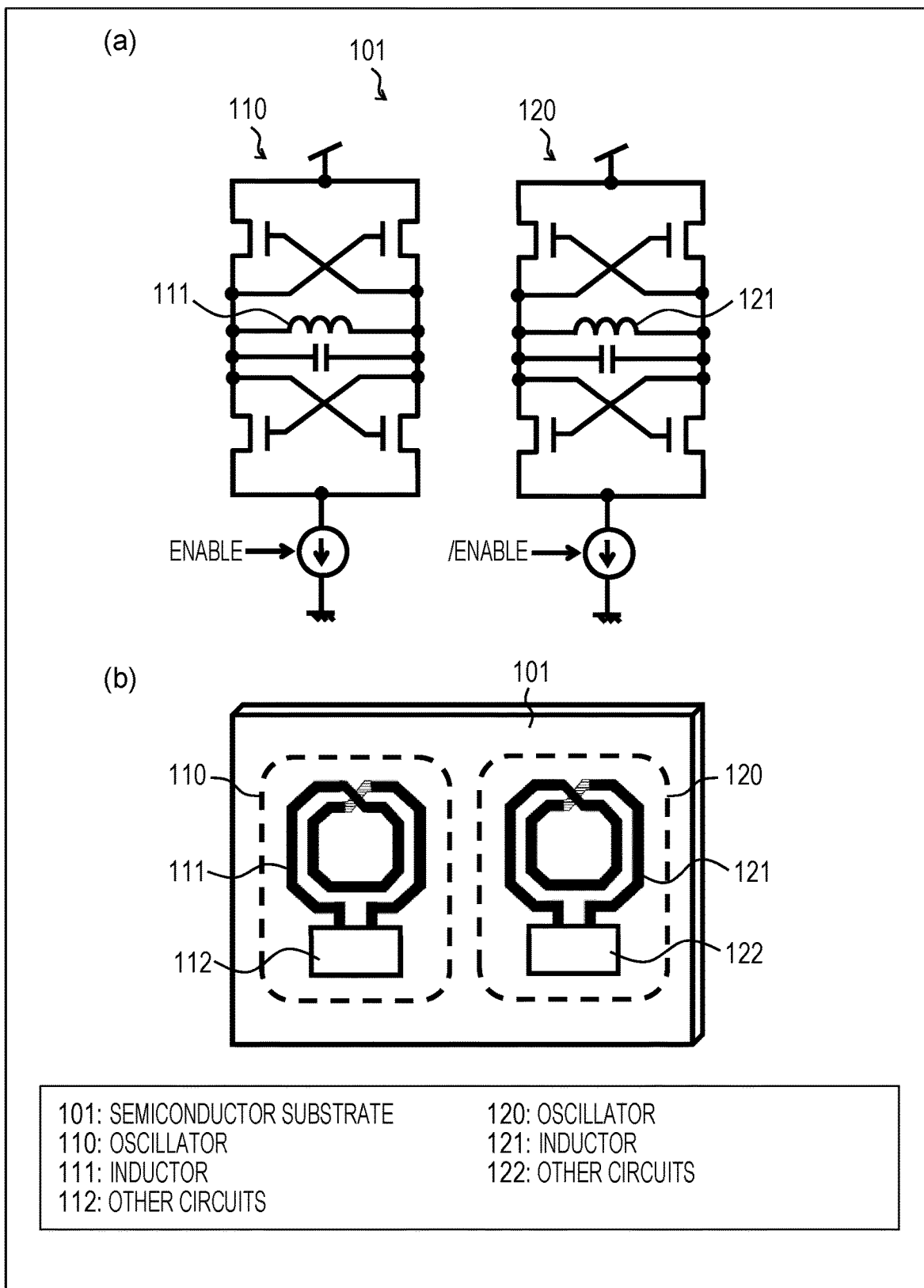
FIG. 7 is a diagram for describing a sensor IC in PTL 1.
Figure 8:
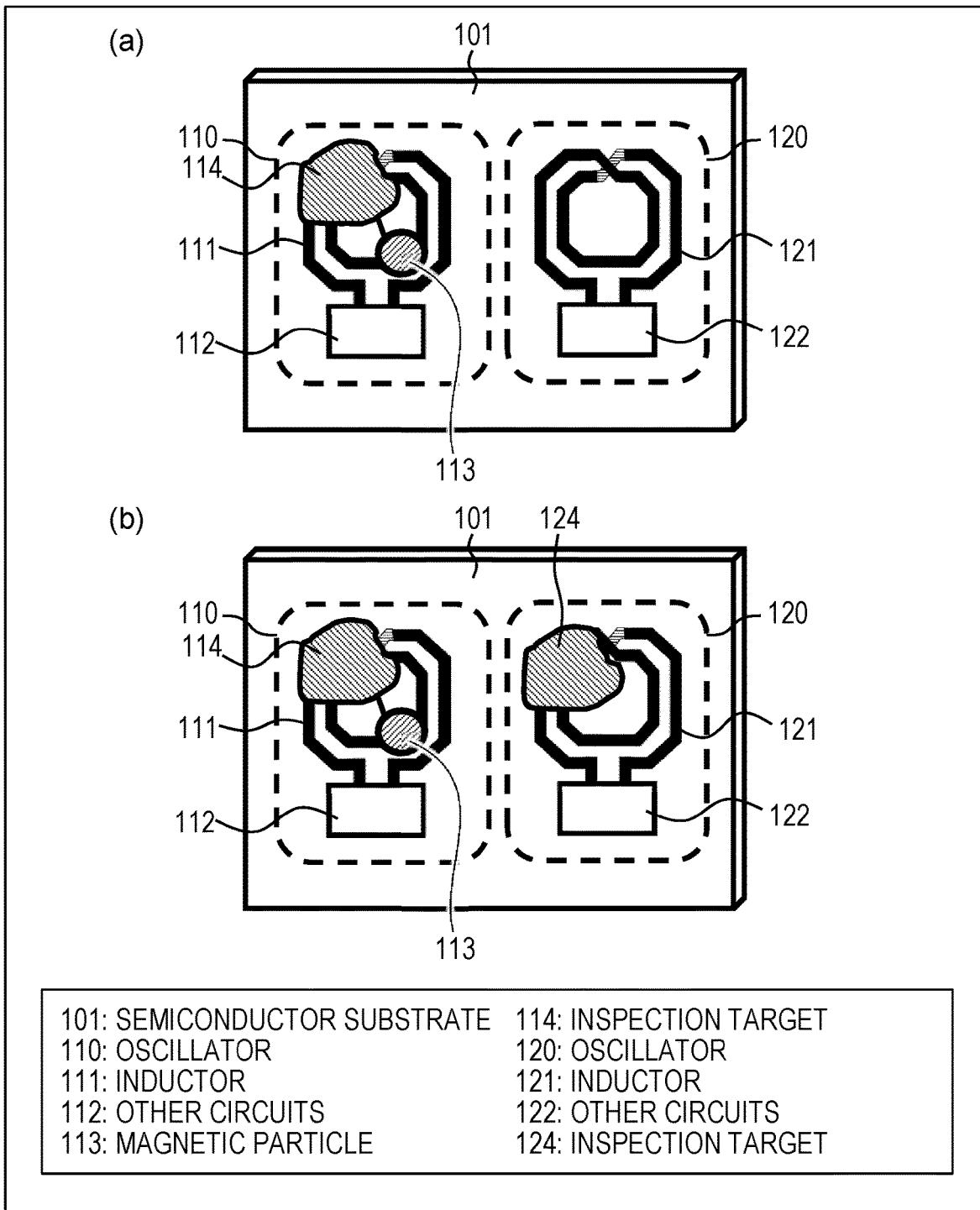
FIG. 8 is a diagram for describing a sensor IC in PTL 1.

FIGS. 5 and 6 illustrate a method for estimating the oscillation frequency by bringing the inspection target into contact with the semiconductor substrate. FIGS. 5(b) and 6(a) respectively illustrate the state in which the inspection targets 76 and 77 are brought into contact with the resonator 50. FIGS. 5(c) and 6(a) respectively illustrate the oscillation frequency of the oscillator 20 in the state illustrated in FIGS. 5(b) and 6(a). The inspection targets 76 and 77 are aqueous solution.

As illustrated in FIG. 5(b), the user brings the inspection target 76 of which the property is not changed (a first state) into uniformly contact with the surface of the semiconductor substrate 10 on which the resonator 50 is formed. Next, the user causes an enable signal to be output to the oscillator 20 from the current source 60.

As a result, the oscillator 20 starts an operation and oscillates at the oscillation frequency in the first state illustrated in FIG. 5(c). The oscillation frequency of the oscillator 20 is divided into 1/N frequency by the frequency divider 30 and is counted for a predetermined period by the detection circuit 3. The detection circuit 3 estimates the oscillation frequency of the oscillator 20 to be the frequency in the first state illustrated in FIG. 5(c), and holds the value of the frequency as the reference frequency.

Thereafter, the property of the inspection target 76 changes to the property of the inspection target 77 (a second state) as illustrated in FIG. 6(a), and as a result thereof, the magnetic permeability (or the dielectric constant) of the inspection target 76 changes to the magnetic permeability (or the dieletric constant) of the water contained in the inspection target 77. In the second state, the user causes an enable signal to be output to the oscillator 20 from the current source 60. As a result, the oscillator 20 starts the operation and oscillates at the oscillation frequency in the second state as illustrated in FIG. 6(b). Similarly to that in the first state, the oscillation frequency of the oscillator 20 in the second state is divided into 1/N frequency by the frequency divider 30 and counted for a predetermined period by the detection circuit 3. Then, the detection circuit 3 estimates that the oscillation frequency of the oscillator 20 is the frequency in the second state illustrated in FIG. 6(b).

As the property of the inspection target 76 changes to that of the inspection target 77, the dielectric constant of the water contained in the inspection targets changes. When the dielectric constant of the water contained in the inspection target changes, the parasitic capacitance value C (or the capacitance value C) applied to the inductor 52 of the resonator 50 changes. The difference ΔC of the capacitance C before and after the change in the property appears as a difference Δf" of the oscillation frequencies of the oscillator 20. The relational expression between the difference Δf" and the difference ΔC is expressed in following Expression 4.

$$\Delta f''=1/\{2\pi\sqrt{(LC)}\}-1/[2\pi\sqrt{(C+\Delta C)}] \qquad \text{Expression 4}$$

(Effects)

The user can estimate that the property of the inspection target 76 is changed to the property of the inspection target 77 by checking the difference Δf" between the reference oscillation frequency in the first state and the oscillation frequency of the oscillator 20 in the second state. An information processing device (a detection unit) may acquire the oscillation frequency of the oscillator 20 estimated by detection circuit 3, and may detected the change in the property of the inspection target with reference to the difference Δf" (change of the oscillation frequency), and furthermore, the user may be notified of the change in the property of inspection target by sending an alarm or the like.

The invention is not limited to each of the mentioned embodiments described above, and various modifications can be made within the scope indicated in the aspects, and also embodiments obtained by appropriately combining technical means respectively disclosed in different embodiments are included in the technical scope of the invention.

In the present embodiment, the MOS transistor is used, but it may be configured with a bipolar transistor. In addition, the inspection target includes all cells and proteins containing the bulk water, inorganic and organic aqueous solution, and the like, and can be applied to this sensor circuit. Furthermore, in this embodiment, the change of the dielectric constant is described as a change in the property of the inspection target such as changing the resonance frequency of the resonator. However, as long as the resonance frequency of the resonator changes due to at least any change of the dielectric constant including the magnetic permeability at a frequency of equal to or higher than 30 GHz and equal to or lower than 200 GHz, the sensor circuit can be applied to the detection of the magnetic permeability or the dielectric constant.

[Summary]

A sensor circuit (1) according to an aspect 1 of the invention is a sensor circuit that inspects property of an inspection target, and includes an oscillation unit (an oscillator 20) having a resonance frequency of 20 to 200 GHz, and an estimation unit (a detection circuit 3) that estimates the oscillation frequency of the oscillation unit.

According to the configuration described above, since the oscillation unit having the resonance frequency of 20 to 200 GHz is used, a change in the oscillation frequency can be detected as a change in the property of the inspection target containing moisture in the vicinity of the oscillation unit. In addition, since magnetic particles are not necessary, procedures for the detection can be reduced.

In the aspect 1, the sensor circuit according to an aspect 2 may further include a detection unit (an information processing device) that detects a change in the property of the inspection target referring to the change in the estimated oscillation frequency.

According to the configuration described above, the detection unit can send an alarm or the like when the change in the property of the inspection target is detected. Therefore, the user can know the change in the property of the inspection target by an alarm or the like sent by the detection unit.

In the aspects 1 or 2, the sensor circuit according to an aspect 3 of the invention may further include a frequency divider that divides the oscillation frequency of the oscillation unit, and may output an output signal having the division-resultant frequency to the estimation unit. The estimation unit may estimate the oscillation frequency of the oscillation unit referring to the output signal of the frequency divider.

A high-speed counter circuit is required for directly detecting the change of the oscillation frequency of equal to or higher than 30 GHz and equal to or lower than 200 GHz of the oscillation unit using a counter circuit. According to the configuration described above, since the operation speed of the counter circuit can be reduced by providing the frequency divider between the oscillation unit and the estimation unit, a change of the signal frequency output from the oscillation unit can be detected with a simple circuit.

In the aspects 1 to 3 in the sensor circuit according to an aspect 4 of the invention, the oscillation unit may include an inductor.

According to the configuration described above, a parasitic capacitance applied to the inductor changes by the changes of the dielectric constant due to the variations of the state of water in the inspection target containing moisture in the vicinity of the inductor of the sensor circuit, and furthermore, the oscillation frequency of the oscillation unit changes. Therefore, it is possible to detect the change of the dielectric constant of the inspection target by checking the change of the oscillation frequency.

In the aspects 1 to 4, in the sensor circuit according to an aspect 5 of the invention, the oscillation unit may include a capacitor.

According to the configuration described above, a capacitance of the capacitor changes by the changes of the dielectric constant due to the variations of the inspection target containing moisture in the vicinity of the capacitor of the sensor circuit, and furthermore, the oscillation frequency of the oscillation unit changes. Therefore, it is possible to detect the change of the dielectric constant of the inspection target by checking the change of the oscillation frequency.

The invention is not limited to each of the mentioned embodiments described above, and various modifications can be made within the scope indicated in the aspects, and also embodiments obtained by appropriately combining technical means respectively disclosed in different embodiments are included in the technical scope of the invention. Furthermore, new technical features can be formed by combining technical means disclosed in each of the embodiments.

REFERENCE SIGNS LIST 1 sensor circuit
3 detection circuit (estimation unit)
20 oscillator (oscillation unit)
30 frequency divider
52 inductor
54 capacitor

The invention claimed is:

1. A sensor circuit for inspecting property of an inspection target containing moisture, comprising:
   a semiconductor substrate;
   an oscillator comprising a cross-coupled transistor and a resonator exposedly formed on a surface of the semiconductor substrate, the oscillator oscillating at a frequency of any of 30 to 200 GHz;
   an counter circuit that counts a frequency of a signal which the oscillator oscillates;
   a sealing material that seals the semiconductor substrate, the sealing material having a window through which the inspection target comes in contact with a surface of the resonator; and
   a detection unit that detects a change in the property of the inspection target referring to a change in the counted frequency.

2. The sensor circuit according to claim 1, further comprising:
   a frequency divider that divides the frequency of the oscillator and outputs an output signal having the division-resultant frequency to the counter circuit,
   wherein the counter circuit counts the frequency of the signal output from the frequency divider for a predetermined period,
   the sensor circuit further comprises an estimation unit comprising the counter circuit which estimates the frequency of the oscillator referring to the counted result of the counter circuit.

3. The sensor circuit according to claim 2,
   wherein the estimation unit estimates the frequency of the oscillator basing on an operation of the oscillator caused by an enable signal.

4. The sensor circuit according to claim 1,
   wherein the oscillator includes an inductor, and the detection unit uses the inductor for detection.

5. The sensor circuit according to claim 1,
   wherein the oscillator includes a capacitor, and the detection unit uses the capacitor for detection.

* * * * *

UNITED STATES PATENT AND TRADEMARK OFFICE
CERTIFICATE OF CORRECTION

PATENT NO. : 10,578,574 B2
APPLICATION NO. : 15/743826
DATED : March 3, 2020
INVENTOR(S) : Takeshi Mitsunaka et al.

Page 1 of 1

It is certified that error appears in the above-identified patent and that said Letters Patent is hereby corrected as shown below:

On the Title Page

Item (30) Foreign Application Priority Data
Should be corrected to:
Jul. 13, 2015 (JP) ................... 2015-139937

Signed and Sealed this
Nineteenth Day of May, 2020

Andrei Iancu
*Director of the United States Patent and Trademark Office*